United States Patent
Yoo et al.

(10) Patent No.: US 12,190,523 B2
(45) Date of Patent: Jan. 7, 2025

(54) ACUTE INTRACRANIAL HEMORRHAGE SEGMENTATION ON BRAIN IMAGES FOR VOLUME QUANTIFICATION AND INDIVIDUAL DETECTION

(71) Applicant: SIEMENS HEALTHINEERS AG, Forchheim (DE)

(72) Inventors: Youngjin Yoo, Princeton, NJ (US); Eli Gibson, Plainsboro, NJ (US); Bogdan Georgescu, Princeton, NJ (US); Gengyan Zhao, Plainsboro, NJ (US); Thomas Re, New York, NY (US); Jyotipriya Das, Plainsboro, NJ (US); Eva Eibenberger, Nuremberg (DE); Andrei Chekkoury, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 394 days.

(21) Appl. No.: 17/651,107

(22) Filed: Feb. 15, 2022

(65) Prior Publication Data
US 2023/0316532 A1     Oct. 5, 2023

(51) Int. Cl.
*G06T 7/12*     (2017.01)
*A61B 6/03*     (2006.01)
(Continued)

(52) U.S. Cl.
CPC ............ *G06T 7/12* (2017.01); *A61B 6/032* (2013.01); *A61B 6/501* (2013.01); *G06T 7/0012* (2013.01);
(Continued)

(58) Field of Classification Search
CPC ........... G06T 7/12; G06T 7/0012; G06T 7/62; G06T 2207/10072; G06T 2207/20081;
(Continued)

(56) References Cited

U.S. PATENT DOCUMENTS

2021/0279887 A1*  9/2021  Ma ............................ G06T 7/12
2022/0020152 A1*  1/2022  Orasanu ................. G06T 7/0014
(Continued)

OTHER PUBLICATIONS

He Xizhi et al: "HMOE-Net: Hybrid Multi-scale Object Equalization Network for Intracerebral Hemorrhage Segmentation in CT Images", 2020 IEEE International Conference on Bioinformatics and Biomedicine (BIBM), IEEE, Dec. 16, 2020 (Dec. 16, 2020), pp. 1006-1009, XP033876199, DOI: 10.1109/BIBM48841.2020. 9313439 [retrieved on Jan. 4, 2021].
(Continued)

*Primary Examiner* — Dhaval V Patel (57) ABSTRACT

Systems and methods for determining a segmentation of a hemorrhage are provided. An input medical image of a hemorrhage of a patient is received. A contour-sensitive segmentation of the hemorrhage from the input medical image is performed using a machine learning based contour-sensitive segmentation network. A detection-sensitive segmentation of the hemorrhage from the input medical image is performed using a machine learning based detection-sensitive segmentation network. A final segmentation of the hemorrhage from the input medical image is determined based on results of the contour-sensitive segmentation and results of the detection-sensitive segmentation. The final segmentation of the hemorrhage is output.

20 Claims, 5 Drawing Sheets

(51) Int. Cl.
*A61B 6/50* (2024.01)
*G06T 7/00* (2017.01)
*G06T 7/62* (2017.01)

(52) U.S. Cl.
CPC ...... *G06T 7/62* (2017.01); *G06T 2207/10072* (2013.01); *G06T 2207/20081* (2013.01); *G06T 2207/20084* (2013.01); *G06T 2207/30016* (2013.01); *G06T 2207/30101* (2013.01)

(58) Field of Classification Search
CPC . G06T 2207/20084; G06T 2207/30016; G06T 2207/30101; G06T 2207/10081; G06T 2207/20221; G06T 2207/30096; G06T 7/11; G06T 2207/10012; G06T 2207/10088; G06T 2207/20112; G06T 2207/30204; A61B 6/032; A61B 6/501; G06N 3/08
See application file for complete search history.

(56) References Cited

U.S. PATENT DOCUMENTS

| | | | | |
|---|---|---|---|---|
| 2023/0316532 A1* | 10/2023 | Yoo | ............................ | G06T 7/12 382/128 |
| 2023/0316699 A1* | 10/2023 | Qi | ........................... | G06V 10/26 382/157 |
| 2023/0368388 A1* | 11/2023 | Xue | ........................ | G06T 7/0012 |
| 2023/0386032 A1* | 11/2023 | Wei | ........................ | G06V 10/82 |

OTHER PUBLICATIONS

Li Xiangyu et al: "The state-of-the-art 3D anisotropic *intracranial hemorrhage segmentation on non-contrast head CT: The Instance challenge", arxiv.org, Cornell University Library, 201 Olin Library Cornell University Ithaca, NY 14853, Jan. 9, 2023 (Jan. 9, 2023), XP091410397.

Matsoukas Stavros et al: "Accuracy of artificial intelligence for the detection of intracranial hemorrhage and chronic cerebral microbleeds: a systematic review and pooled analysis", Medline, US National Library of Medicine (NLM), Bethesda, MD, US, Oct. 1, 2022 (Oct. 1, 2022), XP002808926.

Extended European Search Report (EESR) mailed May 4, 2023 in corresponding European Patent Application No. 23 156 345.3.

Arab et al., "A fast and fully-automated deep-learning approach for accurate hemorrhage segmentation and volume quantification in non-contrast whole-head CT," 2020, Scientific Reports, Issue 10, Article No. 19389, 12 pgs.

Monteiro et al., "Multiclass semantic segmentation and quantification of traumatic brain injury lesions on head CT using deep learning: an algorithm development and multicentre validation study," 2020, The Lancet Digital Health vol. 2, Issue 6, pp. e314-e322.

O'Connor, "Artificial intelligence specialist wins FDA clearance for brain injury CT software," 2021, AI & Emerging Technologies, retrieved online at: https://www.healthimaging.com/topics/ai-emerging-technologies/ai-qureai-fda-clearance-brain-injury-ct, 1 page.

Letter from U.S. Food & Drug Administration Re: "qER-Quant Device," Jul. 30, 2021, retrieved online at: https://www.accessdata.fda.gov/cdrh_docs/pdf21/K211222.pdf, 9 pgs.

Aidoc, "This ICH finding could be easily flagged in your worklist," retrieved online on Nov. 8, 2021, at https://www.aidoc.com/ich-detection/, 1 page.

Utility U.S. Appl. No. 17/249,783, filed Mar. 12, 2021, entitled "Machine Learning for Automatic Detection of Intracranial Hemorrhages with Uncertainty Measures from Ct Images," 35 pgs.

* cited by examiner

ACUTE INTRACRANIAL HEMORRHAGE SEGMENTATION ON BRAIN IMAGES FOR VOLUME QUANTIFICATION AND INDIVIDUAL DETECTION

TECHNICAL FIELD

The present invention relates generally to acute intracranial hemorrhage segmentation on brain images, and in particular to acute intracranial hemorrhage segmentation on brain images for volume quantification and individual detection.

BACKGROUND

Intracranial hemorrhage (ICH) refers to bleeding inside the skull or brain. ICH is commonly caused by a rupture of a blood vessel within the brain. Acute ICH is a potentially life-threatening condition and must be rapidly triaged to mitigate neurological deficit and mortality. In the current clinical practice, acute ICH is manually confirmed by a neuroradiologist evaluating head non-contrast computed tomography (NCCT) imaging. However, such manual evaluation of NCCT imaging is a labor-intensive process requiring subspecialty-trained neuroradiologists. Recently, artificial intelligence-based approaches have been proposed for segmentation and quantification of ICH. However, such artificial intelligence-based approaches do not provide both accurate contouring of ICH segmentations and highly sensitive ICH detection, resulting in reduced accuracy.

BRIEF SUMMARY OF THE INVENTION

In accordance with one or more embodiments, systems and methods for determining a segmentation of a hemorrhage are provided. An input medical image of a hemorrhage of a patient is received. A contour-sensitive segmentation of the hemorrhage from the input medical image is performed using a machine learning based contour-sensitive segmentation network. A detection-sensitive segmentation of the hemorrhage from the input medical image is performed using a machine learning based detection-sensitive segmentation network. A final segmentation of the hemorrhage from the input medical image is determined based on results of the contour-sensitive segmentation and results of the detection-sensitive segmentation. The final segmentation of the hemorrhage is output.

In one embodiment, the machine learning based contour-sensitive segmentation network is trained according to at least one of a soft dice loss or a generalized dice loss and the machine-learning based detection-sensitive segmentation network is trained according to a marginal cross-entropy loss.

In one embodiment, the final segmentation of the hemorrhage is determined by combining the results of the contour-sensitive segmentation and the results of the detection-sensitive segmentation. Bleeding objects are identified in the results of the contour-sensitive segmentation and the results of the detection-sensitive segmentation. The bleeding objects are identified in the results of the contour-sensitive segmentation that match the bleeding objects in the results of the detection-sensitive segmentation. A volume of each of the bleeding objects identified in the results of the contour-sensitive segmentation and in the results of the detection-sensitive segmentation is calculated. The results of the contour-sensitive segmentation and the results of the detection-sensitive segmentation are combined based on the matching bleeding objects and the calculated volumes of the bleeding objects. In one embodiment, the results are combined by selecting one or more of the bleeding objects identified in the results of the detection-sensitive segmentation and replacing the selected one or more bleeding objects in the results of the detection-sensitive segmentation with the matching bleeding object in the results of the contour-sensitive segmentation. The one or more of the bleeding objects may be selected by selecting bleeding objects in the results of the detection-sensitive segmentation that have a calculated volume satisfying a threshold as the one or more bleeding objects or by selecting a top N bleeding objects identified in the results of the detection-sensitive segmentation having a largest volume as the one or more bleeding objects, wherein N is any positive integer.

In one embodiment, the input medical image comprises a 3D computed tomography image of a brain of the patient.

These and other advantages of the invention will be apparent to those of ordinary skill in the art by reference to the following detailed description and the accompanying drawings.

DETAILED DESCRIPTION

The present invention generally relates to methods and systems for acute ICH (intracranial hemorrhage) segmentation on brain images for volume quantification and individual detection. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Conventional artificial intelligence and machine learning based approaches for hemorrhage segmentation provide either accurate contouring of segmented hemorrhages or sensitive detection of hemorrhages, but not both. To address the imbalance performance between accurate ICH volume quantification and ICH detection ability, embodiments described herein provide for ICH segmentation utilizing two segmentation networks: a contouring-sensitive network and a detection-sensitive network. In clinical practice, accurate contouring of large bleeding objects is important for total bleeding volume quantification. On the other hand, accurate contouring of small bleeding objects is less important but their accurate detection can be more clinically useful in managing brain trauma and stroke patients. Accordingly, embodiments described herein provide for both accurate ICH contouring for volume quantification of relatively larger bleeding areas and ICH detection for relatively smaller bleeding areas to provide for effective early intervention. Advantageously, embodiments described herein improve the clinical workflow for evaluating ICH by improving radiologist productivity and accuracy.

Figure 1:
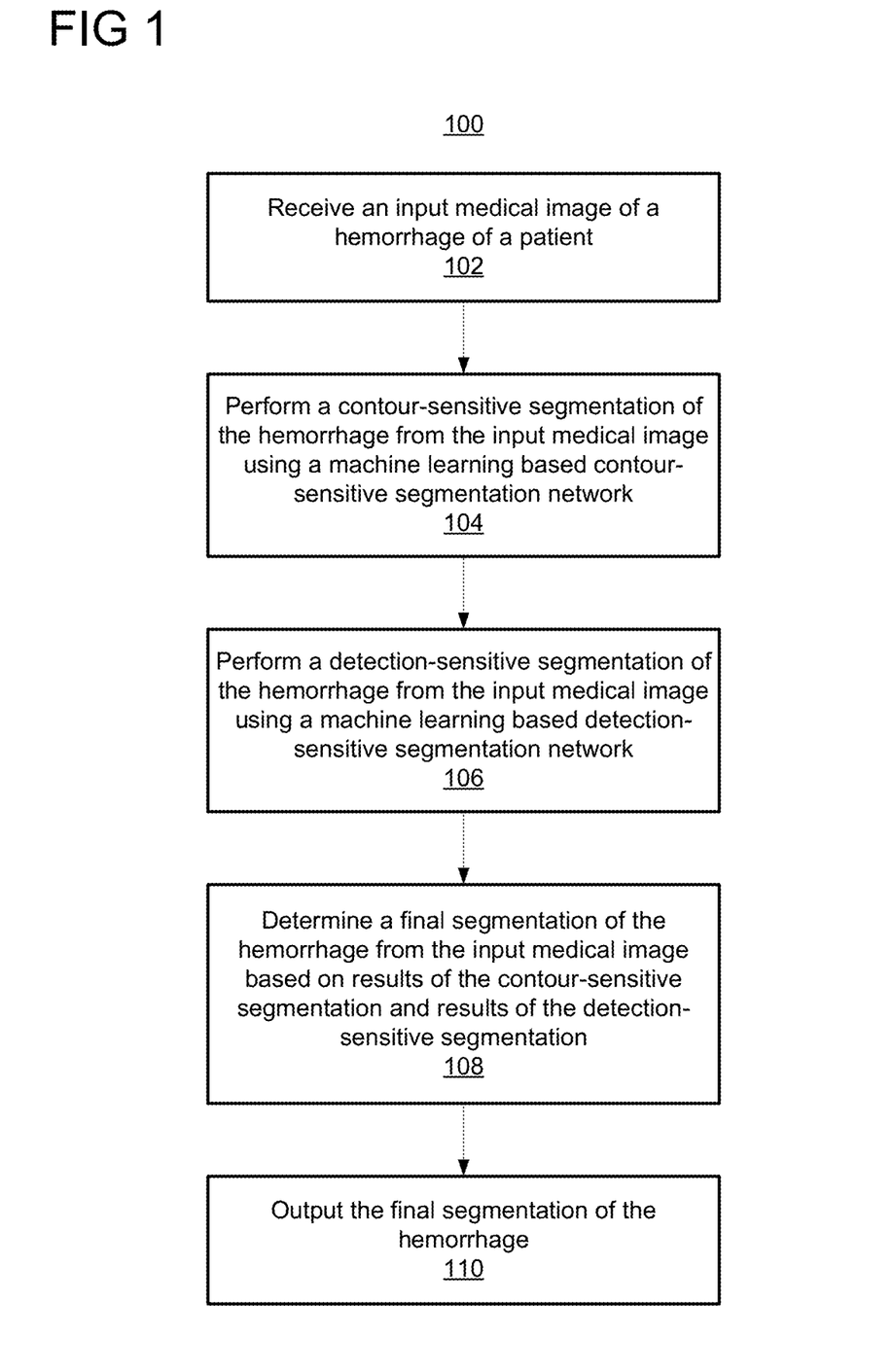
FIG. 1 shows a method for hemorrhage segmentation, in accordance with one or more embodiments.
Figure 2:
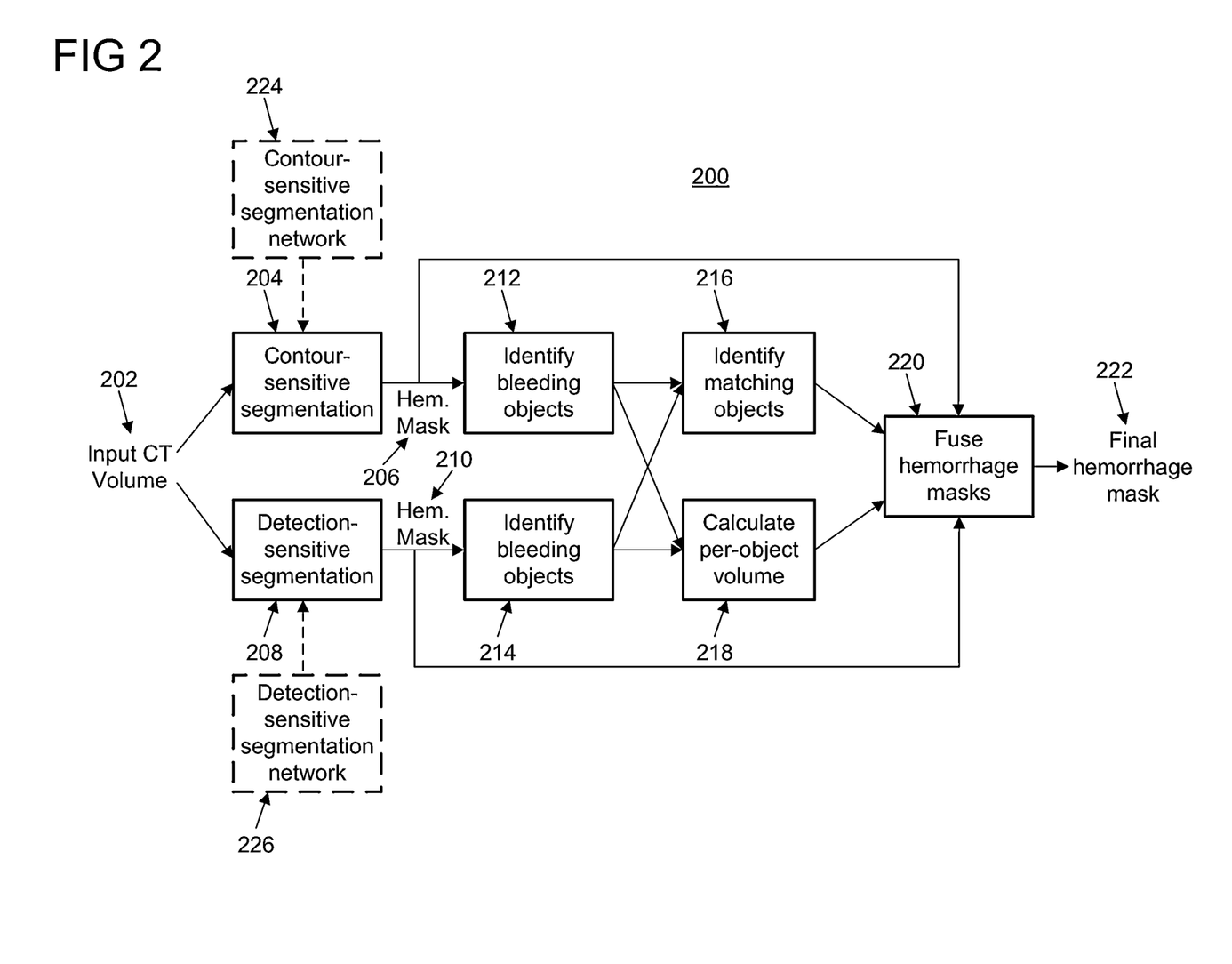
FIG. 2 shows a workflow for hemorrhage segmentation, in accordance with one or more embodiments.

FIG. 1 shows a method 100 for hemorrhage segmentation, in accordance with one or more embodiments. The steps of method 100 may be performed by one or more suitable computing devices, such as, e.g., computer 502 of FIG. 5. FIG. 2 shows a workflow 200 for hemorrhage segmentation, in accordance with one or more embodiments. FIG. 1 and FIG. 2 will be described together.

At step 102 of FIG. 1, an input medical image of a hemorrhage of a patient is received. In one embodiment, the input medical image is of a brain hemorrhage of a brain of the patient.

In one embodiment, the input medical image is a CT (computed tomography) image. For example, as shown in FIG. 2, the input medical image may be input CT volume 202 of workflow 200. However, the input medical image may be of any other suitable modality, such as, e.g., MRI (magnetic resonance imaging), ultrasound, x-ray, or any other medical imaging modality or combinations of medical imaging modalities. The input medical image may be 2D (two dimensional) image or a 3D (three dimensional) volume. It should be understood that reference herein to a pixel of an image may equally apply to a voxel of a volume (and vice versa). The input medical image may comprise a single image or a plurality of images. The input medical image may be received directly from an image acquisition device, such as, e.g., a CT scanner, as the input medical image is acquired, or can be received by loading previously acquired medical images from a storage or memory of a computer system or receiving medical images that have been transmitted from a remote computer system.

At step 104 of FIG. 1, a contour-sensitive segmentation of the hemorrhage from the input medical image is performed using a machine learning based contour-sensitive segmentation network. The contour-sensitive segmentation results in a contour-sensitive hemorrhage segmentation mask with accurate hemorrhage contouring. The contour-sensitive hemorrhage segmentation mask is a pixelwise (or voxelwise) heat map having pixel intensity values ranging from, e.g., 0 to 1 representing a probability that a respective pixel depicts the hemorrhage. The contour-sensitive hemorrhage segmentation mask may be a binary mask generated by applying a predefined threshold to the heat map. In one example, as shown in FIG. 2, the contour-sensitive segmentation is performed as contour-sensitive segmentation 204 to segment a hemorrhage from input CT volume 202 using contour-sensitive segmentation network 224 to generate contour-sensitive hemorrhage segmentation mask 206 in workflow 200.

The contour-sensitive segmentation network is a segmentation network trained to generate segmentations with accurate contouring of the hemorrhage. The contour-sensitive segmentation network may be implemented using any suitable machine learning based segmentation network trained to generate segmentations with accurate contouring of the hemorrhage. For example, the contour-sensitive segmentation network may be a segmentation network trained using a contouring specific loss function, such as, e.g., soft dice loss, generalized dice loss, or any other suitable loss function for accurately segmenting contours of the hemorrhage.

At step 106 of FIG. 1, a detection-sensitive segmentation of the hemorrhage from the input medical image is performed using a machine learning based detection-sensitive segmentation network. The detection-sensitive segmentation results in a detection-sensitive hemorrhage segmentation mask with accurate hemorrhage detection, including of small bleedings that can be critical for timely patient management or early intervention. The detection-sensitive hemorrhage segmentation mask is a pixelwise (or voxelwise) heat map having pixel intensity values ranging from, e.g., 0 to 1 representing a probability that a respective pixel depicts the hemorrhage. The detection-sensitive hemorrhage segmentation mask may be a binary mask generated by applying a predefined threshold to the heat map. In one example, as shown in FIG. 2, the detection-sensitive segmentation is performed as detection-sensitive segmentation 208 to segment a hemorrhage from input CT volume 202 using detection-sensitive segmentation network 226 to generate detection-sensitive hemorrhage segmentation mask 210 in workflow 200.

The detection-sensitive segmentation network is a segmentation network trained to generate segmentations with accurate detections of the hemorrhage. The detection-sensitive segmentation network may be implemented using any suitable machine learning segmentation network trained to generate segmentations with accurate detections of the hemorrhage. For example, the detection-sensitive segmentation network may be a segmentation network trained using a detection specific loss function, such as, e.g., marginal CE (cross-entropy) loss or any other suitable loss function for segmenting the hemorrhage with high detection accuracy. The contour-sensitive segmentation network (applied at step 104) and the detection-sensitive segmentation network may be implementing using the same network architecture or different network architectures.

In one embodiment, the hemorrhage detection may be formulated as an object detection problem solved using object detection networks, such as, e.g., R-CNN (region-based convolutional neural network), fast-R-CNN, faster-R-CNN, mask-R-CNN, YOLO (you only look once), and SSD (single shot detector), which can generate segmentation masks shown detected hemorrhages areas without accurate hemorrhage contouring.

At step 108 of FIG. 1, a final segmentation of the hemorrhage from the input medical image is determined based on results of the contour-sensitive segmentation and results of the detection-sensitive segmentation. The results of the contour-sensitive segmentation may be the contour-sensitive hemorrhage segmentation mask generated by the contour-specific segmentation network and the results of the detection-sensitive segmentation may be the detection-sensitive hemorrhage segmentation mask generated by the detection-sensitive segmentation network. In one embodiment, the final segmentation of the hemorrhage is determined by combining or fusing the results of the contour-sensitive segmentation and results of the detection-sensitive segmentation. For example, the final segmentation of the hemorrhage may be determined by performing a bounding-box based fusion to group clinically meaningful bleeding objects.

A bounding-box based fusion for determining a final segmentation of a hemorrhage is performed in workflow 200 of FIG. 2. At blocks 212 and 214 of FIG. 2, individual bleeding objects are identified in contour-sensitive hemorrhage segmentation mask 206 and detection-sensitive hemorrhage segmentation mask 210. In one embodiment, the individual bleeding objects are identified in the hemorrhage segmentation masks 206 and 210 by a connected component analysis. In a connected component analysis, a label is assigned to each cluster of connected pixels to identify connected components representing the individual bleeding objects. At block 216 of FIG. 2, bleeding objects identified at block 212 from contour-sensitive hemorrhage segmentation mask 206 that match bleeding objects identified at block 214 from detection-sensitive hemorrhage segmentation mask 210 are identified. In one embodiment, a bleeding objects match when a bleeding object identified at block 212 overlaps with a bleeding object identified at block 214. At block 218 of FIG. 2, a per-object volume of each of the bleeding objects identified at blocks 212 and 214 are measured.

At block 220, contour-sensitive hemorrhage segmentation mask 206 and detection-sensitive hemorrhage segmentation mask 210 are fused based on the matching objects identified at block 216 and the volume of the bleeding objects calculated at block 218 to generate a final hemorrhage mask 222. In clinical practice, accurate contouring of large bleeding objects is important for total bleeding volume quantification. On the other hand, accurate contouring of small bleeding objects is less important but their accurate detection can be more clinically useful in managing brain trauma and stroke patients. Accordingly, in one embodiment, to fuse the contour-sensitive hemorrhage segmentation mask 206 and detection-sensitive hemorrhage segmentation mask 210, the detection-sensitive hemorrhage segmentation mask 210 is updated by selecting one or more identified bleeding objects in the detection-sensitive hemorrhage segmentation mask 210 and replacing the selected one or more identified bleeding objects in the detection-sensitive hemorrhage segmentation mask 210 with the matching bleeding object in the contour-sensitive hemorrhage segmentation mask 204. The updated detection-sensitive hemorrhage segmentation mask is output as the final hemorrhage mask 222.

In one embodiment, the one or more identified bleeding objects that are replaced in the detection-sensitive hemorrhage segmentation mask 210 are determined as bleeding objects identified in the detection-sensitive hemorrhage segmentation mask 210 having a volume (calculated at step 218) that is greater than (or otherwise satisfies) a volume threshold. The volume threshold may be determined appropriately according to clinical requirements. In another embodiment, the one or more identified bleeding objects that are replaced in the detection-sensitive hemorrhage segmentation mask 210 are determined as the top N bleeding objects identified in the detection-sensitive hemorrhage segmentation mask 210 having the largest volume, where N is any positive integer. In this embodiment, the bleeding objects identified at block 214 in detection-sensitive hemorrhage segmentation mask 210 are sorted by volume (calculated at block 218) and the top N bleeding objects in the sorted list of bleeding objects are identified. In a further embodiment, the one or more identified bleeding objects that are replaced in the detection-sensitive hemorrhage segmentation mask 210 are determined as the bleeding object identified at block 214 in detection-sensitive hemorrhage segmentation mask 210 having a maximum overlapping ratio with bleeding objects identified at block 212 in contour-sensitive hemorrhage segmentation mask 206. In this embodiment, where there is no overlapping bleeding object, object replacement does not occur.

At step 110 of FIG. 1, the final segmentation of the hemorrhage is output. For example, the final segmentation of the hemorrhage can be output by displaying the final segmentation of the hemorrhage on a display device of a computer system, storing the final segmentation of the hemorrhage on a memory or storage of a computer system, or by transmitting the final segmentation of the hemorrhage to a remote computer system.

Advantageously, embodiments described herein utilize a contour-sensitive segmentation network and a separate detection-sensitive segmentation network to provide accurate contouring of large bleeding areas and sensitive detection for individual small bleeding areas. Embodiments described herein utilize connected component analysis and object-wise volume matching to effective fuse the results of the contour-sensitive segmentation and the results of the detection-sensitive segmentation, to thus provide effective clinical assistance for clinicals to measure bleeding volume quantification/expansion and detect small bleeding areas, which are essential in timely patient management.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 3:
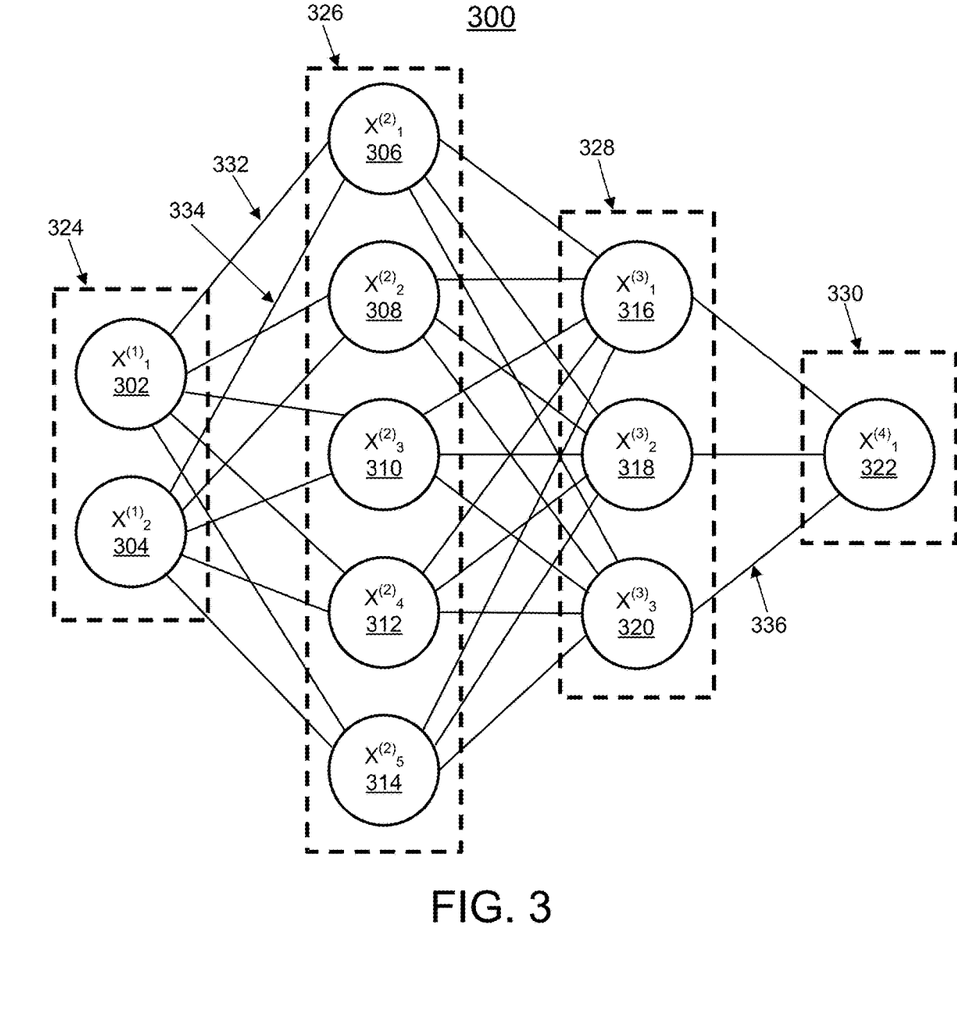
FIG. 3 shows an exemplary artificial neural network that may be used to implement one or more embodiments.

FIG. 3 shows an embodiment of an artificial neural network 300, in accordance with one or more embodiments. Alternative terms for "artificial neural network" are "neural network", "artificial neural net" or "neural net". Machine learning networks described herein, such as, e.g., the contour-sensitive segmentation network and the detection-sensitive segmentation network respectively utilized at steps 104 and 106 of FIG. 1 and contour-sensitive segmentation network 224 and detection-sensitive segmentation network 226 of FIG. 2, may be implemented using artificial neural network 300.

The artificial neural network 300 comprises nodes 302-322 and edges 332, 334, ..., 336, wherein each edge 332, 334, ..., 336 is a directed connection from a first node 302-322 to a second node 302-322. In general, the first node 302-322 and the second node 302-322 are different nodes 302-322, it is also possible that the first node 302-322 and the second node 302-322 are identical. For example, in FIG. 3, the edge 332 is a directed connection from the node 302 to the node 306, and the edge 334 is a directed connection from the node 304 to the node 306. An edge 332, 334, ..., 336 from a first node 302-322 to a second node 302-322 is also denoted as "ingoing edge" for the second node 302-322 and as "outgoing edge" for the first node 302-322.

In this embodiment, the nodes 302-322 of the artificial neural network 300 can be arranged in layers 324-330, wherein the layers can comprise an intrinsic order introduced by the edges 332, 334, ..., 336 between the nodes 302-322. In particular, edges 332, 334, ..., 336 can exist only between neighboring layers of nodes. In the embodiment shown in FIG. 3, there is an input layer 324 comprising only nodes 302 and 304 without an incoming edge, an output layer 330 comprising only node 322 without outgoing edges, and hidden layers 326, 328 in-between the input layer 324 and the output layer 330. In general, the number of hidden layers 326, 328 can be chosen arbitrarily. The number of nodes 302 and 304 within the input layer 324 usually relates to the number of input values of the neural network 300, and the number of nodes 322 within the output layer 330 usually relates to the number of output values of the neural network 300.

In particular, a (real) number can be assigned as a value to every node 302-322 of the neural network 300. Here, x(n); denotes the value of the i-th node 302-322 of the n-th layer 324-330. The values of the nodes 302-322 of the input layer 324 are equivalent to the input values of the neural network 300, the value of the node 322 of the output layer 330 is equivalent to the output value of the neural network 300. Furthermore, each edge 332, 334, ..., 336 can comprise a weight being a real number, in particular, the weight is a real number within the interval [−1, 1] or within the interval [0, 1]. Here, $w^{(m,n)}_{i,j}$ denotes the weight of the edge between the i-th node 302-322 of the m-th layer 324-330 and the j-th node 302-322 of the n-th layer 324-330. Furthermore, the abbreviation $w^{(n)}_{i,j}$ is defined for the weight $w^{(n,n+1)}_{i,j}$.

In particular, to calculate the output values of the neural network 300, the input values are propagated through the neural network. In particular, the values of the nodes 302-322 of the (n+1)-th layer 324-330 can be calculated based on the values of the nodes 302-322 of the n-th layer 324-330 by $$x_j^{(n+1)} = f\left(\sum_i x_i^{(n)} \cdot w_{i,j}^{(n)}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 324 are given by the input of the neural network 300, wherein values of the first hidden layer 326 can be calculated based on the values of the input layer 324 of the neural network, wherein values of the second hidden layer 328 can be calculated based in the values of the first hidden layer 326, etc.

In order to set the values $w^{(m,n)}_{i,j}$ for the edges, the neural network 300 has to be trained using training data. In particular, training data comprises training input data and training output data (denoted as $t_i$). For a training step, the neural network 300 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 300 (backpropagation algorithm). In particular, the weights are changed according to $$w'^{(n)}_{i,j} = w^{(n)}_{i,j} - \gamma \cdot \delta^{(n)}_j \cdot x_i^{(n)}$$

wherein $\gamma$ is a learning rate, and the numbers $\delta^{(n)}_j$ can be recursively calculated as $$\delta^{(n)}_j = \left(\sum_k \delta_k^{(n+1)} \cdot w_{j,k}^{(n+1)}\right) \cdot f'\left(\sum_i x_i^{(n)} \cdot w_{i,j}^{(n)}\right)$$

based on $\delta^{(n+1)}_j$, if the (n+1)-th layer is not the output layer, and $$\delta^{(n)}_j = \left(x_k^{(n+1)} - t_j^{(n+1)}\right) \cdot f'\left(\sum_i x_i^{(n)} \cdot w_{i,j}^{(n)}\right)$$

if the (n+1)-th layer is the output layer 330, wherein f' is the first derivative of the activation function, and $y^{(n+1)}_j$ is the comparison training value for the j-th node of the output layer 330.

Figure 4:
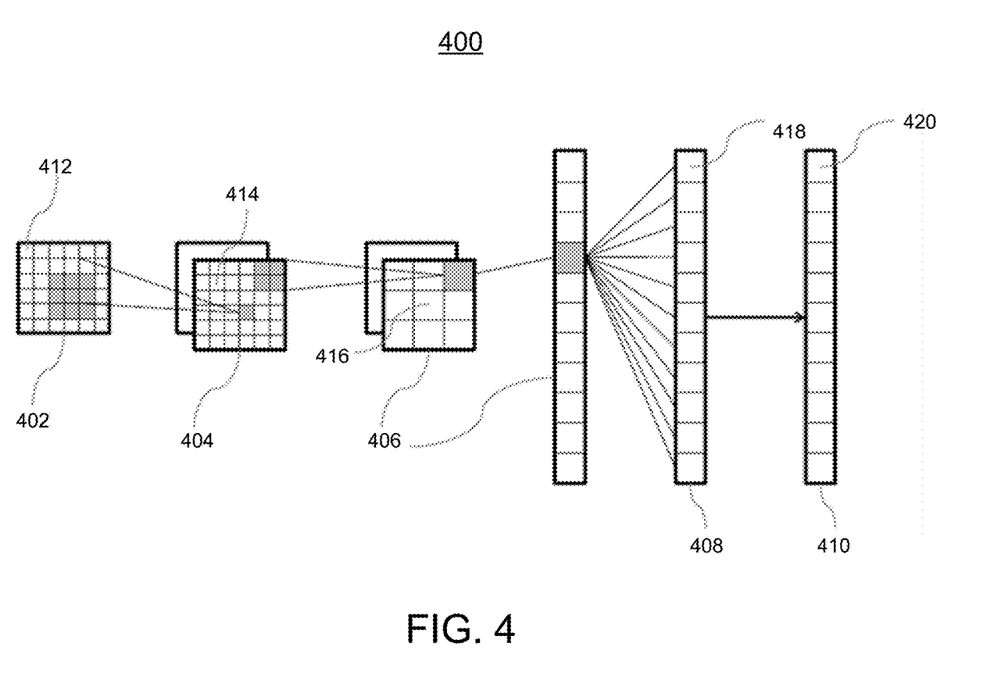
FIG. 4 shows a convolutional neural network that may be used to implement one or more embodiments.

FIG. 4 shows a convolutional neural network 400, in accordance with one or more embodiments. Machine learning networks described herein, such as, e.g., the contour-sensitive segmentation network and the detection-sensitive segmentation network respectively utilized at steps 104 and 106 of FIG. 1 and contour-sensitive segmentation network 224 and detection-sensitive segmentation network 226 of FIG. 2, may be implemented using convolutional neural network 400.

In the embodiment shown in FIG. 4, the convolutional neural network comprises 400 an input layer 402, a convolutional layer 404, a pooling layer 406, a fully connected layer 408, and an output layer 410. Alternatively, the convolutional neural network 400 can comprise several convolutional layers 404, several pooling layers 406, and several fully connected layers 408, as well as other types of layers.

The order of the layers can be chosen arbitrarily, usually fully connected layers 408 are used as the last layers before the output layer 410.

In particular, within a convolutional neural network 400, the nodes 412-420 of one layer 402-410 can be considered to be arranged as a d-dimensional matrix or as a d-dimensional image. In particular, in the two-dimensional case the value of the node 412-420 indexed with i and j in the n-th layer 402-410 can be denoted as x(n) [i]. However, the arrangement of the nodes 412-420 of one layer 402-410 does not have an effect on the calculations executed within the convolutional neural network 400 as such, since these are given solely by the structure and the weights of the edges.

In particular, a convolutional layer 404 is characterized by the structure and the weights of the incoming edges forming a convolution operation based on a certain number of kernels. In particular, the structure and the weights of the incoming edges are chosen such that the values $x^{(n)}_k$ of the nodes 414 of the convolutional layer 404 are calculated as a convolution $x^{(n)}_k = K_k * x^{(n-1)}$ based on the values $x^{(n-1)}$ of the nodes 412 of the preceding layer 402, where the convolution * is defined in the two-dimensional case as $$x^{(n)}_k[i,j] = (K_k * x^{(n-1)})[i,j] = \sum_{i'} \sum_{j'} K_k[i',j'] \cdot x^{(n-1)}[i-i', j-j'].$$

Here the k-th kernel $K_k$ is a d-dimensional matrix (in this embodiment a two-dimensional matrix), which is usually small compared to the number of nodes 412-418 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 412-420 in the respective layer 402-410. In particular, for a convolutional layer 404, the number of nodes 414 in the convolutional layer is equivalent to the number of nodes 412 in the preceding layer 402 multiplied with the number of kernels.

If the nodes 412 of the preceding layer 402 are arranged as a d-dimensional matrix, using a plurality of kernels can be interpreted as adding a further dimension (denoted as "depth" dimension), so that the nodes 414 of the convolutional layer 404 are arranged as a (d+1)-dimensional matrix. If the nodes 412 of the preceding layer 402 are already arranged as a (d+1)-dimensional matrix comprising a depth dimension, using a plurality of kernels can be interpreted as expanding along the depth dimension, so that the nodes 414 of the convolutional layer 404 are arranged also as a (d+1)-dimensional matrix, wherein the size of the (d+1)-dimensional matrix with respect to the depth dimension is by a factor of the number of kernels larger than in the preceding layer 402.

The advantage of using convolutional layers 404 is that spatially local correlation of the input data can exploited by enforcing a local connectivity pattern between nodes of adjacent layers, in particular by each node being connected to only a small region of the nodes of the preceding layer.

In embodiment shown in FIG. 4, the input layer 402 comprises 36 nodes 412, arranged as a two-dimensional 6×6 matrix. The convolutional layer 404 comprises 72 nodes 414, arranged as two two-dimensional 6×6 matrices, each of the two matrices being the result of a convolution of the values of the input layer with a kernel. Equivalently, the nodes 414 of the convolutional layer 404 can be interpreted as arranges as a three-dimensional 6×6×2 matrix, wherein the last dimension is the depth dimension.

A pooling layer 406 can be characterized by the structure and the weights of the incoming edges and the activation function of its nodes 416 forming a pooling operation based on a non-linear pooling function f. For example, in the two dimensional case the values x(n) of the nodes 416 of the pooling layer 406 can be calculated based on the values $x^{(n-1)}$ of the nodes 414 of the preceding layer 404 as $$x^{(n)}[i,j] = f(x^{(n-1)}[id_1, jd_2], \ldots, x^{(n-1)}[id_1+d_1-1, jd_2+d_2-1])$$

In other words, by using a pooling layer 406, the number of nodes 414, 416 can be reduced, by replacing a number d1·d2 of neighboring nodes 414 in the preceding layer 404 with a single node 416 being calculated as a function of the values of said number of neighboring nodes in the pooling layer. In particular, the pooling function f can be the max-function, the average or the L2-Norm. In particular, for a pooling layer 406 the weights of the incoming edges are fixed and are not modified by training.

The advantage of using a pooling layer 406 is that the number of nodes 414, 416 and the number of parameters is reduced. This leads to the amount of computation in the network being reduced and to a control of overfitting.

In the embodiment shown in FIG. 4, the pooling layer 406 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 408 can be characterized by the fact that a majority, in particular, all edges between nodes 416 of the previous layer 406 and the nodes 418 of the fully-connected layer 408 are present, and wherein the weight of each of the edges can be adjusted individually.

In this embodiment, the nodes 416 of the preceding layer 406 of the fully-connected layer 408 are displayed both as two-dimensional matrices, and additionally as non-related nodes (indicated as a line of nodes, wherein the number of nodes was reduced for a better presentability). In this embodiment, the number of nodes 418 in the fully connected layer 408 is equal to the number of nodes 416 in the preceding layer 406. Alternatively, the number of nodes 416, 418 can differ.

Furthermore, in this embodiment, the values of the nodes 420 of the output layer 410 are determined by applying the Softmax function onto the values of the nodes 418 of the preceding layer 408. By applying the Softmax function, the sum the values of all nodes 420 of the output layer 410 is 1, and all values of all nodes 420 of the output layer are real numbers between 0 and 1.

A convolutional neural network 400 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 400 can be trained based on the backpropagation algorithm. For preventing overfitting, methods of regularization can be used, e.g. dropout of nodes 412-420, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1 or 2. Certain steps or functions of the methods and workflows described herein, including one or more of the steps or functions of FIG. 1 or 2, may be performed by a server or by another processor in a network-based cloud-computing system. Certain steps or functions of the methods and workflows described herein, including one or more of the steps of FIG. 1 or 2, may be performed by a client computer in a network-based cloud computing system. The steps or functions of the methods and workflows described herein, including one or more of the steps of FIG. 1 or 2, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1 or 2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
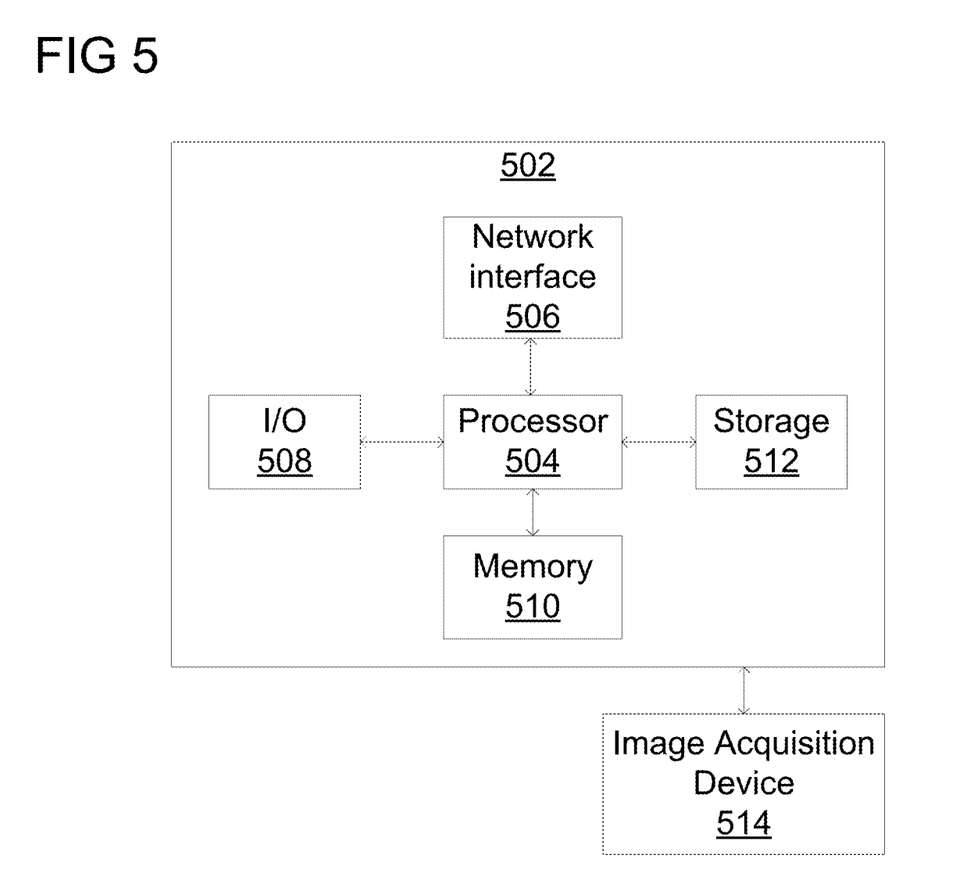
FIG. 5 shows a high-level block diagram of a computer that may be used to implement one or more embodiments.

A high-level block diagram of an example computer 502 that may be used to implement systems, apparatus, and methods described herein is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method and workflow steps or functions of FIG. 1 or 2 can be defined by the computer program instructions stored in memory 510 and/or data storage device 512 and controlled by processor 504 executing the computer program instructions. For example, the computer program instructions can be implemented as computer executable code programmed by one skilled in the art to perform the method and workflow steps or functions of FIG. 1 or 2. Accordingly, by executing the computer program instructions, the processor 504 executes the method and workflow steps or functions of FIG. 1 or 2. Computer 502 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

An image acquisition device 514 can be connected to the computer 502 to input image data (e.g., medical images) to the computer 502. It is possible to implement the image acquisition device 514 and the computer 502 as one device. It is also possible that the image acquisition device 514 and the computer 502 communicate wirelessly through a network. In a possible embodiment, the computer 502 can be located remotely with respect to the image acquisition device 514.

Any or all of the systems and apparatus discussed herein may be implemented using one or more computers such as computer 502.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
   receiving an input medical image of a hemorrhage of a patient;
   performing a contour-sensitive segmentation of the hemorrhage from the input medical image using a machine learning based contour-sensitive segmentation network;
   performing a detection-sensitive segmentation of the hemorrhage from the input medical image using a machine learning based detection-sensitive segmentation network;
   determining a final segmentation of the hemorrhage from the input medical image based on results of the contour-sensitive segmentation and results of the detection-sensitive segmentation; and
   outputting the final segmentation of the hemorrhage.

2. The computer-implemented method of claim 1, wherein the machine learning based contour-sensitive segmentation network is trained according to at least one of a soft dice loss or a generalized dice loss.

3. The computer-implemented method of claim 1, wherein the machine learning based detection-sensitive segmentation network is trained according to a marginal cross-entropy loss.

4. The computer-implemented method of claim 1, wherein determining a final segmentation of the hemorrhage from the input medical image based on results of the contour-sensitive segmentation and results of the detection-sensitive segment comprises:
   combining the results of the contour-sensitive segmentation and the results of the detection-sensitive segmentation.

5. The computer-implemented method of claim 4, wherein combining the results of the contour-sensitive segmentation and the results of the detection-sensitive segmentation comprises:
   identifying bleeding objects in the results of the contour-sensitive segmentation and the results of the detection-sensitive segmentation;
   identifying the bleeding objects in the results of the contour-sensitive segmentation that match the bleeding objects in the results of the detection-sensitive segmentation;
   calculating a volume of each of the bleeding objects identified in the results of the contour-sensitive segmentation and in the results of the detection-sensitive segmentation; and
   combining the results of the contour-sensitive segmentation and the results of the detection-sensitive segmentation based on the matching bleeding objects and the calculated volumes of the bleeding objects.

6. The computer-implemented method of claim 5, wherein combining the results of the contour-sensitive segmentation and the results of the detection-sensitive segmentation based on the matching bleeding objects and the calculated volumes of the bleeding objects comprises:
   selecting one or more of the bleeding objects identified in the results of the detection-sensitive segmentation; and
   replacing the selected one or more bleeding objects in the results of the detection-sensitive segmentation with the matching bleeding object in the results of the contour-sensitive segmentation.

7. The computer-implemented method of claim 6, wherein selecting one or more of the bleeding objects identified in the results of the detection-sensitive segmentation comprises:
   selecting bleeding objects in the results of the detection-sensitive segmentation that have a calculated volume satisfying a threshold as the one or more bleeding objects.

8. The computer-implemented method of claim 6, wherein selecting one or more of the bleeding objects identified in the results of the detection-sensitive segmentation comprises:
   selecting a top N bleeding objects identified in the results of the detection-sensitive segmentation having a largest volume as the one or more bleeding objects, wherein N is any positive integer.

9. The computer-implemented method of claim 1, wherein the input medical image comprises a 3D computed tomography image of a brain of the patient.

10. An apparatus comprising:
    means for receiving an input medical image of a hemorrhage of a patient;
    means for performing a contour-sensitive segmentation of the hemorrhage from the input medical image using a machine learning based contour-sensitive segmentation network;
    means for performing a detection-sensitive segmentation of the hemorrhage from the input medical image using a machine learning based detection-sensitive segmentation network;
    means for determining a final segmentation of the hemorrhage from the input medical image based on results of the contour-sensitive segmentation and results of the detection-sensitive segmentation; and
    means for outputting the final segmentation of the hemorrhage.

11. The apparatus of claim 10, wherein the machine learning based contour-sensitive segmentation network is trained according to at least one of a soft dice loss or a generalized dice loss.

12. The apparatus of claim 10, wherein the machine learning based detection-sensitive segmentation network is trained according to a marginal cross-entropy loss.

13. The apparatus of claim 10, wherein the means for determining a final segmentation of the hemorrhage from the input medical image based on results of the contour-sensitive segmentation and results of the detection-sensitive segment comprises:
    means for combining the results of the contour-sensitive segmentation and the results of the detection-sensitive segmentation.

14. The apparatus of claim 10, wherein the input medical image comprises a 3D computed tomography image of a brain of the patient.

15. A non-transitory computer readable medium storing computer program instructions, the computer program instructions when executed by a processor cause the processor to perform operations comprising:
    receiving an input medical image of a hemorrhage of a patient;
    performing a contour-sensitive segmentation of the hemorrhage from the input medical image using a machine learning based contour-sensitive segmentation network;
    performing a detection-sensitive segmentation of the hemorrhage from the input medical image using a machine learning based detection-sensitive segmentation network;
    determining a final segmentation of the hemorrhage from the input medical image based on results of the contour-sensitive segmentation and results of the detection-sensitive segmentation; and
    outputting the final segmentation of the hemorrhage.

16. The non-transitory computer readable medium of claim 15, wherein determining a final segmentation of the hemorrhage from the input medical image based on results of the contour-sensitive segmentation and results of the detection-sensitive segment comprises:
    combining the results of the contour-sensitive segmentation and the results of the detection-sensitive segmentation.

17. The non-transitory computer readable medium of claim 16, wherein combining the results of the contour-sensitive segmentation and the results of the detection-sensitive segmentation comprises:
    identifying bleeding objects in the results of the contour-sensitive segmentation and the results of the detection-sensitive segmentation;
    identifying the bleeding objects in the results of the contour-sensitive segmentation that match the bleeding objects in the results of the detection-sensitive segmentation;
    calculating a volume of each of the bleeding objects identified in the results of the contour-sensitive segmentation and in the results of the detection-sensitive segmentation; and
    combining the results of the contour-sensitive segmentation and the results of the detection-sensitive segmentation based on the matching bleeding objects and the calculated volumes of the bleeding objects.

18. The non-transitory computer readable medium of claim 17, wherein combining the results of the contour-sensitive segmentation and the results of the detection-sensitive segmentation based on the matching bleeding objects and the calculated volumes of the bleeding objects comprises:
    selecting one or more of the bleeding objects identified in the results of the detection-sensitive segmentation; and
    replacing the selected one or more bleeding objects in the results of the detection-sensitive segmentation with the matching bleeding object in the results of the contour-sensitive segmentation.

19. The non-transitory computer readable medium of claim 18, wherein selecting one or more of the bleeding objects identified in the results of the detection-sensitive segmentation comprises:
    selecting bleeding objects in the results of the detection-sensitive segmentation that have a calculated volume satisfying a threshold as the one or more bleeding objects.

20. The non-transitory computer readable medium of claim 18, wherein selecting one or more of the bleeding objects identified in the results of the detection-sensitive segmentation comprises:
    selecting a top N bleeding objects identified in the results of the detection-sensitive segmentation having a largest volume as the one or more bleeding objects, wherein N is any positive integer.

* * * * *